(12) United States Patent
Michihata et al.

(10) Patent No.: US 10,952,597 B2
(45) Date of Patent: Mar. 23, 2021

(54) ENDOSCOPE APPARATUS AND METHOD OF DETECTING EDGE

(71) Applicant: Sony Olympus Medical Solutions Inc., Tokyo (JP)

(72) Inventors: Taihei Michihata, Kanagawa (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 580 days.

(21) Appl. No.: 15/877,234

(22) Filed: Jan. 22, 2018

(65) Prior Publication Data

US 2018/0242830 A1 Aug. 30, 2018

(30) Foreign Application Priority Data

Feb. 24, 2017 (JP) .............................. JP2017-033937

(51) Int. Cl.
| A61B 1/05 | (2006.01) |
| A61B 1/00 | (2006.01) |
| A61B 1/04 | (2006.01) |
| A61B 1/045 | (2006.01) |
| A61B 1/06 | (2006.01) |

(52) U.S. Cl.
CPC .......... *A61B 1/053* (2013.01); *A61B 1/00006* (2013.01); *A61B 1/00009* (2013.01); *A61B 1/0019* (2013.01); *A61B 1/00039* (2013.01); *A61B 1/00105* (2013.01); *A61B 1/00188* (2013.01); *A61B 1/00195* (2013.01); *A61B 1/042* (2013.01); *A61B 1/045* (2013.01); *A61B 1/00147* (2013.01); *A61B 1/0661* (2013.01)

(58) Field of Classification Search
USPC .......................................................... 600/112
See application file for complete search history.

(56) References Cited

U.S. PATENT DOCUMENTS

| 5,929,901 A * | 7/1999 | Adair ................. A61B 1/00135 257/E25.032 |
| 2006/0232684 A1* | 10/2006 | Miki ...................... H04N 9/735 348/223.1 |
| 2011/0160534 A1* | 6/2011 | Lee .......................... A61B 1/04 600/109 |
| 2013/0135454 A1* | 5/2013 | Ito ...................... H04N 5/23212 348/77 |

(Continued)

FOREIGN PATENT DOCUMENTS

| JP | 2001-128059 A | 5/2001 |
| JP | 2001-327466 A | 11/2001 |
| JP | 2015-134039 | 7/2015 |

*Primary Examiner* — Michael J Carey
*Assistant Examiner* — Minqiao Huang
(74) *Attorney, Agent, or Firm* — Xsensus LLP (57) ABSTRACT

An endoscope apparatus includes a camera and circuitry. The camera is detachably connected to a base of an endoscope adapted to be inserted in a subject and includes a sensor configured to image a subject image captured by the endoscope. The circuitry is configured to process an image captured by the camera and generate a video signal for display, calculate a gain in white balance based on the captured image, and perform mask edge detecting processing for detecting a boundary point between the subject image and a mask area other than the subject image included in the captured image.

11 Claims, 6 Drawing Sheets

(56) References Cited

U.S. PATENT DOCUMENTS

| | | | |
|---|---|---|---|
| 2013/0286202 A1* | 10/2013 | Wu ................... | H04N 5/23241 |
| | | | 348/143 |
| 2013/0321706 A1* | 12/2013 | Nakamura ........... | H04N 1/6027 |
| | | | 348/655 |
| 2014/0240533 A1* | 8/2014 | Hirooka ................ | H04N 9/646 |
| | | | 348/223.1 |
| 2015/0065803 A1* | 3/2015 | Douglas ................... | G06T 7/11 |
| | | | 600/200 |
| 2015/0208015 A1* | 7/2015 | Takahashi .......... | G06K 9/00369 |
| | | | 348/159 |
| 2015/0243027 A1* | 8/2015 | Ichiki ...................... | A61B 1/04 |
| | | | 382/128 |
| 2015/0243033 A1* | 8/2015 | Uemori ................... | G06T 7/254 |
| | | | 382/103 |
| 2016/0344992 A1* | 11/2016 | D'Alfonso ......... | A61B 1/00006 |

* cited by examiner

ENDOSCOPE APPARATUS AND METHOD OF DETECTING EDGE

CROSS-REFERENCE TO RELATED APPLICATION

The present application claims priority to and incorporates by reference the entire contents of Japanese Patent Application No. 2017-033937 filed in Japan on Feb. 24, 2017.

BACKGROUND

The present disclosure relates to an endoscope apparatus and a method of detecting an edge, the endoscope apparatus including an imaging device attachably and detachably connected to an eye contact portion of the endoscope inserted in a subject and having an imaging unit imaging the subject image captured by the endoscope and a control device processing the captured image obtained through imaging by the imaging unit and generating a video signal for display.

Known image processing apparatuses are known that process a captured image of the inside (the inside of a live body) of a subject such as a human body (for example, see Japanese Laid-open Patent Publication No. 2015-134039). The image processing apparatus described in Japanese Laid-open Patent Publication No. 2015-134039 obtains a captured image including a subject image captured by an endoscope inserted into a live body. A light (a subject image) captured by the endoscope has a substantially circular sectional surface. The subject image in the captured image is therefore in a substantially circular shape. The captured image includes a subject image and a mask area other than the subject image. The image processing apparatus converts the captured image into a luminance image and detects a boundary point between the subject image and the mask area using luminance distribution in the luminance image.

SUMMARY

In detecting a boundary point between a subject image and a mask area, if the subject is, for example, a white subject such as gauze, the luminance value of the subject image included in the captured image is sufficiently high. This configuration allows more accurate detection of the boundary point between the subject image and the mask area using the luminance distribution on the captured image. On the other hand, in detecting a boundary point between a subject image and a mask area, use of another subject other than the above-described subject causes a great deal of variation among the luminance values on the subject image included in the captured image. In this case, it is difficult to accurately detect a boundary point between the subject image and the mask area using the luminance distribution in the captured image. The technique described in Japanese Laid-open Patent Publication No. 2015-134039 specifies no subjects in detecting a boundary point between a subject image and a mask area. This technique thus has difficulty in accurately detecting a boundary point between a subject image and a mask area.

An endoscope apparatus according to one aspect of the present disclosure may include: an imaging device detachably connected to an eye contact portion of an endoscope adapted to be inserted in a subject, the imaging device including an imaging unit configured to image a subject image captured by the endoscope; a control device configured to process an image captured by the imaging unit and generate a video signal for display; an operation receiving unit configured to receive a user operation for calculating a gain in white balance; a gain calculating unit configured to calculate the gain in white balance based on the captured image in response to the user operation; and an edge detecting unit configured to perform mask edge detecting processing for detecting a boundary point between the subject image and a mask area other than the subject image included in the captured image in response to the user operation.

DETAILED DESCRIPTION

Embodiments (hereinafter, embodiments) will now be described with reference to the drawings. It should be noted that the following embodiments are not intended to limit the scope of the present disclosure. In the drawings, like numerals indicate like components.

Figure 1:
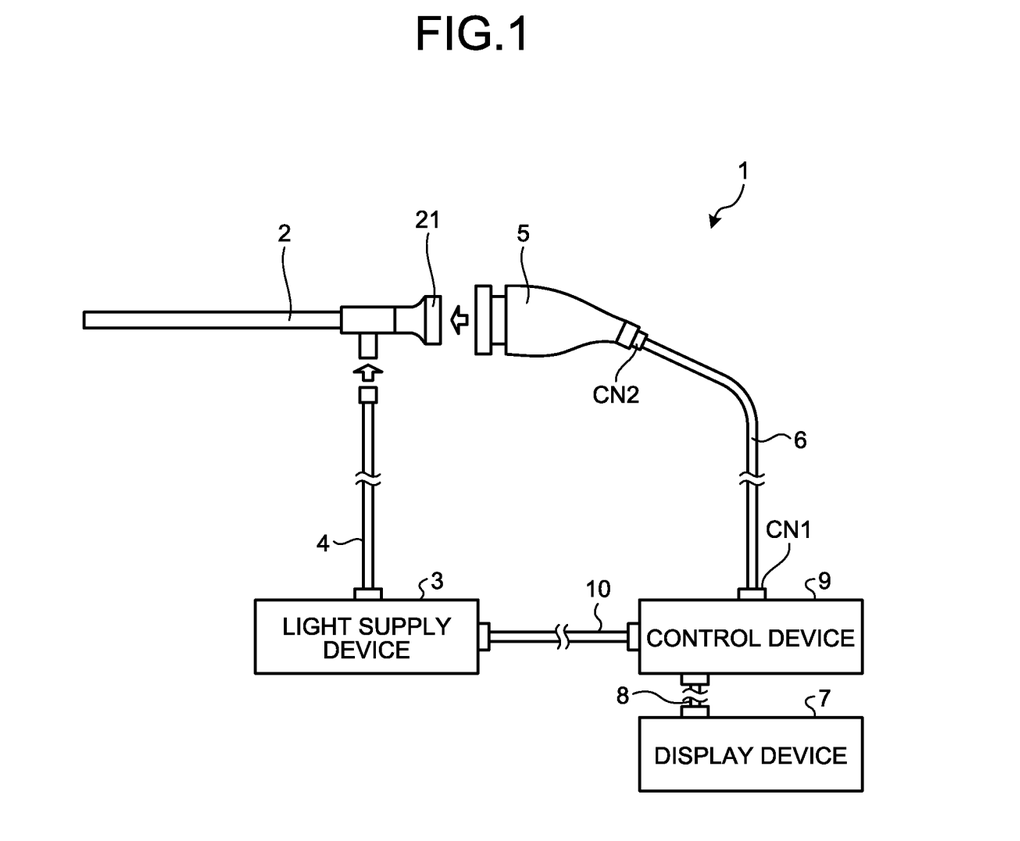
FIG. 1 is a drawing that illustrates a schematic configuration of an endoscope apparatus according to an embodiment.

Schematic configuration of endoscope apparatus FIG. 1 is a drawing that illustrates a schematic configuration of an endoscope apparatus 1 according to an embodiment. The endoscope apparatus 1 is used in the medical field and observes the inside of a live body. As illustrated in FIG. 1, the endoscope apparatus 1 includes an insertion unit 2, a light supply device 3, a light guide 4, a camera head 5, a first transfer cable 6, a display device 7, a second transfer cable 8, a control device 9, and a third transfer cable 10.

The insertion unit 2 is constituted as a rigid endoscope. More specifically, the insertion unit 2 is rigid or at least partly flexible in an elongated shape and is inserted in a live body. The inside of the insertion unit 2 is provided with an optical system consisting of one or a plurality of lenses and gathering light of a subject image. The light supply device 3 has an end of the light guide 4 connected thereto and supplies light for lighting the inside of the live body to the end of the light guide 4 under control of the control device 9. The light guide 4 has an end attachably and detachably connected to the light supply device 3 and has the other end attachably and detachably connected to the insertion unit 2. The light guide 4 transfers light supplied from the light supply device 3 from an end to the other end and supplies the light to the insertion unit 2. The light supplied to the insertion unit 2 is emitted from the front end of the insertion unit 2 and enters the inside of the live body. The light (the subject image) entering the inside of the live body and reflected in the live body is gathered by the optical system in the insertion unit 2.

The camera head 5 functions as an imaging device according to the present disclosure. The camera head 5 is attachably and detachably connected to the base end (an eye contact portion 21 in FIG. 1) of the insertion unit 2. The camera head 5 captures the subject image gathered by the insertion unit 2 in the form of a light and outputs an image signal (RAW signal) obtained through the imaging under control of the control device 9. Examples of the image signal include a 4K or higher image signal. The configuration of the camera head 5 will be described later in detail.

The first transfer cable 6 has an end attachably and detachably connected to the control device 9 through a connector CN1 (FIG. 1) and has the other end attachably and detachably connected to the camera head 5 through a connector CN2 (FIG. 1). The first transfer cable 6 transfers an image signal and others output from the camera head 5 to the control device 9 and transfers a control signal, a synchronization signal, a clock, electric power, and others output from the control device 9 to the camera head 5. The camera head 5 may transfer an image signal and others to the control device 9 through the first transfer cable 6 using an optical signal or an electric signal. The control device 9 may transfer a control signal, a synchronization signal, and a clock to the camera head 5 through the first transfer cable 6 in the same manner.

The display device 7 is constituted as a liquid crystal display, an organic electro luminescence (EL) display, or the like and displays an image based on a video signal transmitted from the control device 9 under control of the control device 9. The second transfer cable 8 has an end attachably and detachably connected to the display device 7 and has the other end attachably and detachably connected to the control device 9. The second transfer cable 8 transfers a video signal processed by the control device 9 to the display device 7.

The control device 9 includes a central processing unit (CPU) and others and integrally controls operation of the light supply device 3, the camera head 5, and the display device 7. The configuration of the control device 9 will be described later in detail. The third transfer cable 10 has an end attachably and detachably connected to the light supply device 3 and has the other end attachably and detachably connected to the control device 9. The third transfer cable 10 transfers a control signal received from the control device 9 to the light supply device 3.

Configuration of Camera Head

Figure 2:
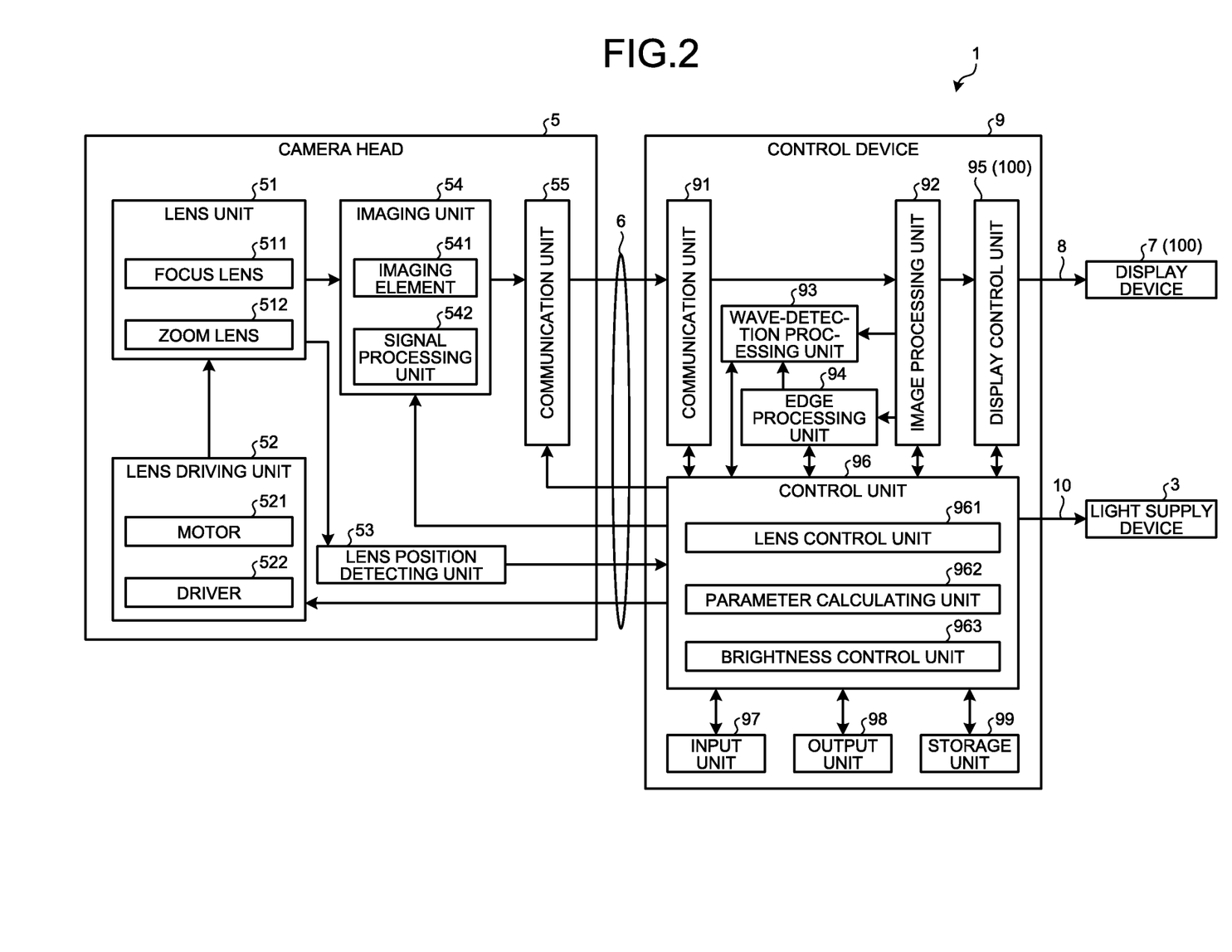
FIG. 2 is a block diagram that illustrates configurations of a camera head and a control device.

The configuration of the camera head 5 will now be described. FIG. 2 is a block diagram that illustrates configurations of the camera head 5 and the control device 9. In FIG. 2, the connectors CN1 and CN2 respectively connecting between the control device 9 and the first transfer cable 6 and connecting between the camera head 5 and the first transfer cable 6, connectors respectively connecting between the control device 9 and the second transfer cable 8 and connecting between the display device 7 and the second transfer cable 8, and connectors respectively connecting between the control device 9 and the third transfer cable 10 and connecting between the light supply device 3 and the third transfer cable 10 are not illustrated for convenience. As illustrated in FIG. 2, the camera head 5 includes a lens unit 51, a lens driving unit 52, a lens position detecting unit 53, an imaging unit 54, and a communication unit 55.

The lens unit 51 is constituted of a plurality of lenses movable along an optical axis and forms a subject image, the light of which is gathered by the insertion unit 2, on an imaging surface of the imaging unit 54 (an imaging element 541 (FIG. 2)). As illustrated in FIG. 2, the lens unit 51 includes a focus lens 511 and a zoom lens 512. The focus lens 511 is constituted of one of or a plurality of lenses and adjusts the focal point by moving along the optical axis. The zoom lens 512 is constituted of one of or a plurality of lenses and adjusts the angle of view by moving along the optical axis. The lens unit 51 is further provided with a focus mechanism (not illustrated) moving the focus lens 511 along the optical axis and an optical zoom mechanism (not illustrated) moving the zoom lens 512 along the optical axis. As illustrated in FIG. 2, the lens driving unit 52 includes a motor 521 operating the above-described focus mechanism and optical zoom mechanism and a driver 522 driving the motor 521. The lens driving unit 52 adjusts the focal point and the angle of view of the lens unit 51 under control of the control device 9.

The lens position detecting unit 53 is constituted as a position sensor such as a photointerrupter and detects the lens position (hereinafter, the focus position) of the focus lens 511 and the lens position (hereinafter, the zoom position) of the zoom lens 512. The lens position detecting unit 53 outputs a detection signal based on the focus position and the zoom position to the control device 9 through the first transfer cable 6.

The imaging unit 54 images the inside of a live body under control of the control device 9. As illustrated in FIG. 2, the imaging unit 54 includes the imaging element 541 and a signal processing unit 542. The imaging element 541 is constituted as a charge coupled device (CCD), a complementary metal oxide semiconductor (CMOS), or the like that receives a subject image gathered by the insertion unit 2 in the form of a light and formed by the lens unit 51 and converts the light to an electric signal (analog signal). The signal processing unit 542 performs signal processing on the electric signal (analog signal) received from the imaging element 541 and outputs an image signal (RAW signal (digital signal)). For example, the signal processing unit 542 performs, on the electric signal (analog signal) from the imaging element 541, signal processing such as processing of removing reset noise, processing of multiplying the analog signal by an analog gain for amplification of the analog signal, and analog to digital conversion.

The communication unit 55 functions as a transmitter transmitting an image signal (RAW signal (digital signal)) output from the imaging unit 54 to the control device 9 through the first transfer cable 6. The communication unit 55 is constituted as a high-speed serial interface that transmits an image signal to the control device 9 at a transfer rate of one Gbps or greater through the first transfer cable 6.

Configuration of Control Device

The configuration of the control device 9 will now be described with reference to FIG. 2. As illustrated in FIG. 2, the control device 9 includes a communication unit 91, an image processing unit 92, a wave-detection processing unit 93, an edge processing unit 94, a display control unit 95, a control unit 96, an input unit 97, an output unit 98, and a storage unit 99. The communication unit 91 functions as a receiver that receives an image signal (RAW signal (digital signal)) output from the camera head 5 (the communication unit 55) through the first transfer cable 6. The communication unit 91 is constituted as a high-speed serial interface that receives an image signal from the communication unit 55 at a transfer rate of one Gbps or greater.

The image processing unit 92 processes the image signal (RAW signal (digital signal)) output from the camera head 5 (the communication unit 55) and received by the communication unit 91 under control of the control unit 96. For example, the image processing unit 92 multiplies the image signal (RAW signal (digital signal)) by a digital gain for amplification of the digital signal. The image processing unit 92 performs RAW processing such as optical black subtraction processing and demosaic processing on the image signal (RAW signal (digital signal)) multiplied by the digital gain and converts the RAW signal (image signal) to an RGB signal (image signal). The image processing unit 92 further performs RGB processing such as white balance adjustment processing for multiplying RGB values by respective gains, RGB gamma correction, and YC conversion (converting an RGB signal (image signal) to a luminance signal and a color difference signal (Y, $C_B/C_R$ signal)) on the RGB signal. The image processing unit 92 further performs YC processing such as color difference correction and noise reduction on the Y, $C_B/C_R$ signal (image signal).

The wave-detection processing unit 93 inputs the image signal (Y, $C_B/C_R$ signal) processed by the image processing unit 92 and performs wave-detection processing based on the image signal (Y, $C_B/C_R$ signal). For example, based on pixel information (a luminance signal (Y signal)) of each pixel in a certain area (hereinafter, a wave-detection area) in the whole captured image in one frame captured by the imaging element 541, the wave-detection processing unit 93 carries out detection of contrast and frequency components of the image in the wave-detection area, detection of the average luminance value and the maximum and minimum pixels in the wave-detection area using a filter and the like, comparison with a threshold, and detection of a histogram and others. The wave-detection processing unit 93 outputs wave-detection information (such as contrast, a frequency component, the average luminance value, the maximum and minimum pixels, and a histogram) obtained through the detection to the control unit 96.

Figure 3:
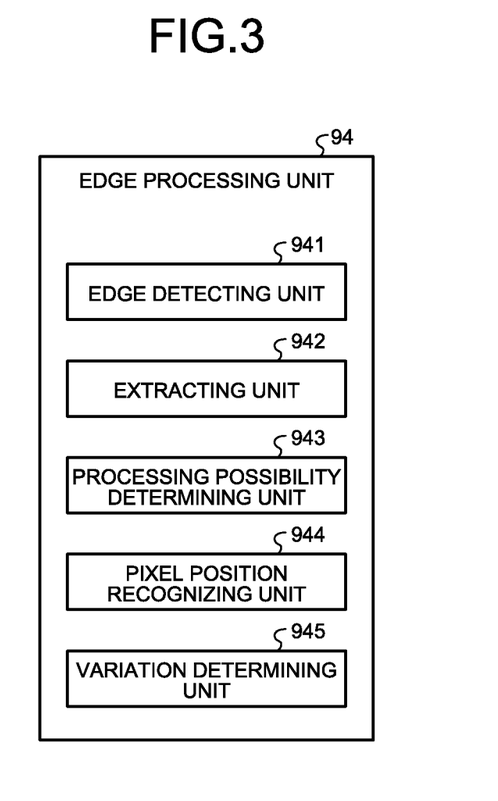
FIG. 3 is a block diagram that illustrates a configuration of an edge processing unit.

FIG. 3 is a block diagram that illustrates a configuration of the edge processing unit 94. The edge processing unit 94 performs mask edge detecting processing and first and second determination processing based on a luminance signal (Y signal) constituting the image signal (Y, $C_B/C_R$ signal) processed by the image processing unit 92. As illustrated in FIG. 3, the edge processing unit 94 includes an edge detecting unit 941, an extracting unit 942, a processing possibility determining unit 943, a pixel position recognizing unit 944, and a variation determining unit 945.

Figure 4:
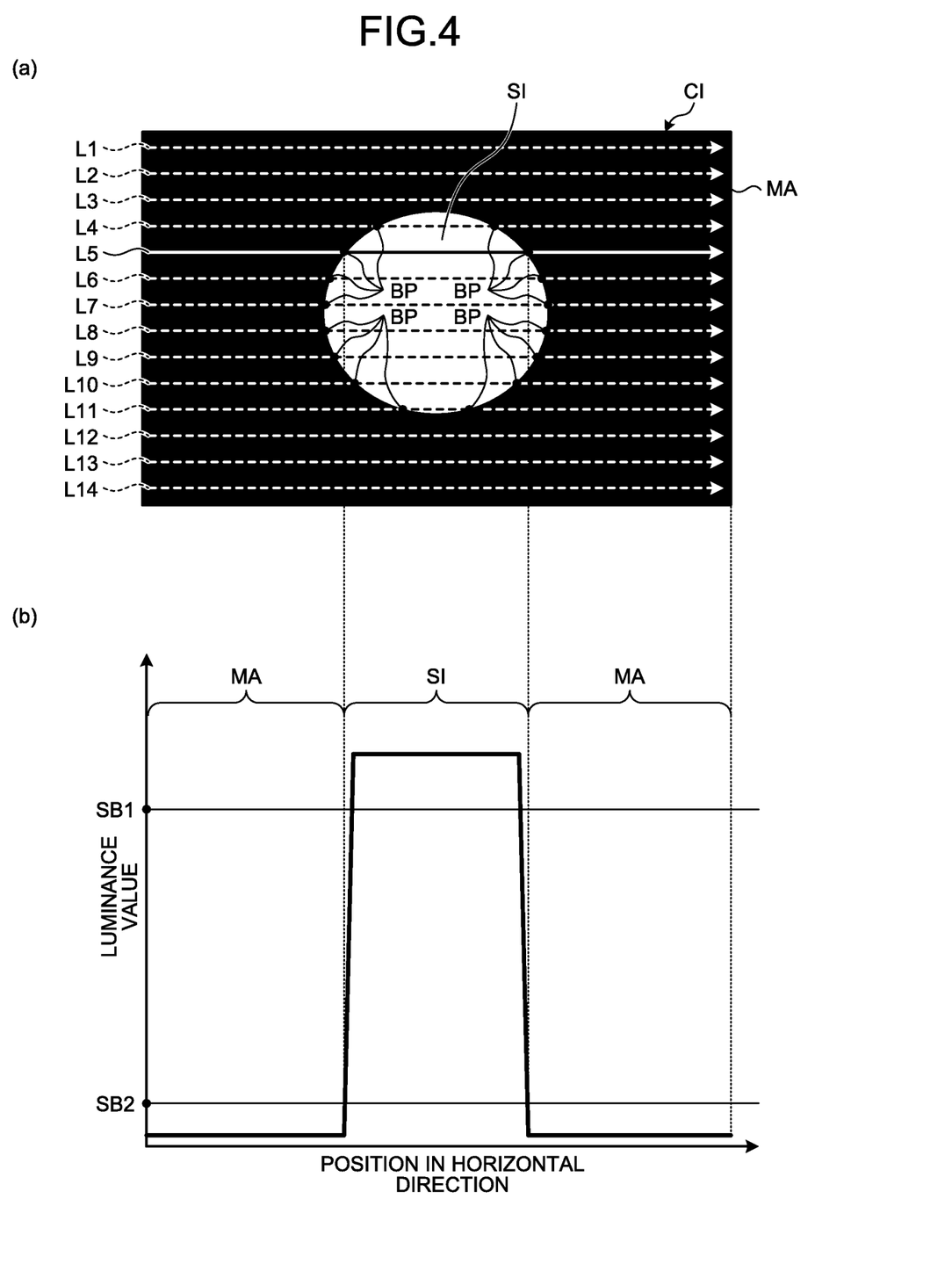
FIG. 4 is an illustrative drawing of mask edge detecting processing.

The edge detecting unit 941 performs the following mask edge detecting processing in response to a user operation (hereinafter, white balance setting operation) to the input unit 97 for having a gain (a gain used in the white balance adjustment processing performed by the image processing unit 92) in white balance calculated according to a result of determination of the first determination processing performed by the processing possibility determining unit 943. FIG. 4 is an illustrative drawing of mask edge detecting processing. More specifically, (a) of FIG. 4 is a drawing that illustrates an exemplary captured image CI captured by the imaging element 541. (b) of FIG. 4 is a drawing that illustrates distribution of luminance values on a horizontal line L5 in the captured image CI of (a) of FIG. 4. A light (a subject image) reflected in a live body and gathered into the insertion unit 2 has a substantially circular sectional surface. A subject image SI in the captured image CI is thus substantially circular as illustrated in (a) of FIG. 4. The captured image CI includes the subject image SI and a mask area (the black area in (a) of FIG. 4) MA other than the subject image SI. The edge detecting unit 941 performs mask edge detecting processing and detects a boundary point BP ((a) of FIG. 4) between the subject image SI and the mask area MA.

More specifically, as illustrated in (a) of FIG. 4, the edge detecting unit 941 acquires a luminance signal (Y signal) of image signals (Y, $C_B/C_R$ signals) processed by the image processing unit 92. The edge detecting unit 941 detects distribution of luminance values on each of a plurality of (14 lines in this embodiment) horizontal lines L1 to L14 in the captured image CI based on the luminance signal (Y signal). On the captured image CI, the area of the subject image SI has higher luminance values than those in the mask area MA. As illustrated in (b) of FIG. 4, in regard to the luminance distribution on the horizontal line L5, the luminance values are high in the part between two boundary points BP, each of which is set between the subject image SI and the mask area MA, and low in other parts. The edge detecting unit 941 compares the luminance values with a first luminance threshold SB1 ((b) of FIG. 4) and recognizes an area having contiguous pixels with higher luminance values than the first luminance threshold SB1 as the subject image SI. The edge detecting unit 941 further compares the luminance values with a second threshold SB2 ((b) of FIG. 4) lower than the first luminance threshold SB1 and recognizes an area having contiguous pixels with lower luminance values than the second luminance threshold SB2 as the mask area MA. The edge detecting unit 941 recognizes the boundary point BP ((a) of FIG. 4) between the subject image SI and the mask area MA. The edge detecting unit 941 performs this processing on each of the horizontal lines L1 to L14 and recognizes a plurality of boundary points BP between the subject image SI and the mask area MA.

The extracting unit 942 acquires a luminance signal (Y signal) of image signals (Y, $C_B/C_R$ signals) processed by the image processing unit 92. The extracting unit 942 compares the luminance value of each pixel on the horizontal line L7 ((a) of FIG. 4) positioned in the center of the captured image CI with the first luminance threshold SB1 based on the luminance signal (Y signal) and extracts first pixels with higher luminance values than the first luminance threshold SB1. The extracting unit 942 further compares each luminance value on the horizontal line L7 with the second luminance threshold SB2 and extracts second pixels with lower luminance values than the second luminance threshold SB2.

The processing possibility determining unit 943 performs the following first determination processing. The processing possibility determining unit 943 compares the number of first pixels (hereinafter, a first contiguous pixel number N1 (see FIG. 6) extracted by the extracting unit 942 and contiguously aligned on the horizontal line L7 with a first pixel number threshold SN1 (see (a) of FIG. 6) and determines whether the image is in a processing possible state that the first contiguous pixel number N1 is equal to or greater than the first pixel number threshold SN1 or in a processing impossible state that the first contiguous pixel number N1 is less than the first pixel number threshold SN1. The processing possibility determining unit 943 further compares the number of second pixels (hereinafter, a second contiguous pixel number N2 (see FIG. 6) extracted by the extracting unit 942 and contiguously aligned on the horizontal line L7 with a second pixel number threshold SN2 (see (a) of FIG. 6) and determines whether the image is in a processing possible state that the second contiguous pixel number N2 is equal to or greater than the second pixel number threshold SN2 or in a processing impossible state that the second contiguous pixel number N2 is less than the second pixel number threshold SN2. The processing possibility determining unit 943 outputs a detection signal according to the result of determination in the first determination processing to the control unit 96.

When the processing possibility determining unit 943 determines the image to be in a processing possible state, the pixel position recognizing unit 944 recognizes the pixel positions of second pixels in which the second contiguous pixel number N2 is equal to or greater than the second pixel number threshold SN2. The variation determining unit 945 performs the following second determination processing. The variation determining unit 945 determines whether all the pixels in the pixel positions recognized by the pixel position recognizing unit 944 are contiguously extracted as the second pixels by the extracting unit 942 after the mask edge detecting processing by the edge detecting unit 941.

The display control unit 95 generates a video signal for display where an image (which corresponds to warning information according to the present disclosure) including a message such as "retry white balance setting operation" is overlapped on the captured image CI based on the image signal (Y, $C_B/C_R$ signal) processed by the image processing unit 92 by using, for example, on-screen display (OSD) processing under control of the control unit 96. The display control unit 95 outputs the video signal to the display device 7 through the second transfer cable 8. In other words, the display control unit 95 and the display device 7 function as warning information notifying units 100 (FIG. 2) according to the present disclosure.

The control unit 96 is constituted of a CPU and others. The control unit 96 controls operation of the light supply device 3, the camera head 5, and the display device 7 by outputting control signals through the first to the third transfer cables 6, 8, and 10 and integrally controls operation of the control device 9. As illustrated in FIG. 2, the control unit 96 includes a lens control unit 961, a parameter calculating unit 962, and brightness control unit 963. The lens control unit 961 operates the lens driving unit 52 and adjusts (changes the focus position and the zoom position) the focal point and the angle of view of the lens unit 51. For example, the lens control unit 961 calculates a focusing evaluation value for evaluating a focusing status of the subject image SI included in the captured image CI based on wave-detection information (such as contrast and frequency components) output from the wave-detection processing unit 93. The lens control unit 961 determines the contrast detected by the wave-detection processing unit 93 or the sum of high frequency components of the frequency components detected by the wave-detection processing unit 93 to be a focusing evaluation value. A greater focusing evaluation value indicates more accurate focusing. The lens control unit 961 thereafter performs AF processing for positioning the focus lens 511 in a focus position where the subject image SI comes to be in a focusing status using, for example, the hill climbing based on the focus position detected by the lens position detecting unit 53 and the focusing evaluation value. The AF processing may be continuous AF in which the processing is continuously performed or one-touch AF in which the processing is performed in response to operation of an operation button (not illustrated) provided to the camera head 5 or the like.

The parameter calculating unit 962 calculates a brightness parameter for changing brightness of the captured image CI obtained through imaging by the imaging unit 54 to reference brightness (changing the average luminance value obtained in the wave-detection processing to a reference average luminance value) based on the wave-detection information (the average luminance value) output from the wave-detection processing unit 93. In this embodiment, the parameter calculating unit 962 calculates four brightness parameters including an exposure time of each pixel of the imaging element 541, an analog gain multiplied by the signal processing unit 542, a digital gain multiplied by the image processing unit 92, the amount of light supplied from the light supply device 3 to the insertion unit 2 based on the wave-detection information (the average luminance value) output from the wave-detection processing unit 93. The parameter calculating unit 962 further calculates respective gains by which the RGB values are multiplied in the white balance adjustment processing performed by the image processing unit 92 based on the wave-detection information output from the wave-detection processing unit 93. The parameter calculating unit 962 outputs a control signal to the image processing unit 92 and determines the calculated gains to be gains by which the RGB values are multiplied in the white balance adjustment processing performed by the image processing unit 92. The parameter calculating unit 962 functions as a gain calculating unit according to the present disclosure.

The brightness control unit 963 controls operation of the imaging element 541, the signal processing unit 542, the image processing unit 92, and the light supply device 3 based on the brightness parameters calculated by the parameter calculating unit 962. More specifically, the brightness control unit 963 outputs a control signal to the imaging unit 54 through the first transfer cable 6 and determines the exposure time (a brightness parameter) calculated by the parameter calculating unit 962 to be the exposure time of each pixel of the imaging element 541. The brightness control unit 963 outputs a control signal to the imaging unit 54 through the first transfer cable 6 and determines the analog gain (a brightness parameter) calculated by the parameter calculating unit 962 to be the analogue gain multiplied by the signal processing unit 542. The brightness control unit 963 outputs a control signal to the image processing unit 92 and determines the digital gain (a brightness parameter) calculated by the parameter calculating unit 962 to be the digital gain multiplied by the image processing unit 92. Furthermore, the brightness control unit 963 outputs a control signal to the light supply device 3 through the third transfer cable 10 and determines the amount of light (a brightness parameter) calculated by the parameter calculating unit 962 to be the amount of light supplied from the light supply device 3 to the insertion unit 2. As described above, the brightness control unit 963 controls operation of the imaging element 541, the signal processing unit 542, the image processing unit 92, and the light supply device 3, whereby brightness of the captured image CI is changed to the reference brightness.

The input unit 97 is constituted as an operation device such as a mouse, a keyboard, and a touch panel and receives a user operation (for example, white balance setting operation) of a user, for example, a doctor. The input unit 97 outputs an operation signal according to the user operation to the control unit 96. The input unit 97 functions as an operation receiving unit according to the present disclosure. The output unit 98 is constituted as a speaker, a printer, and others and outputs various kinds of information. The storage unit 99 stores a program executed by the control unit 96, information necessary for processing performed by the control unit 96, and others.

Operation of Endoscope Apparatus

Figure 5:
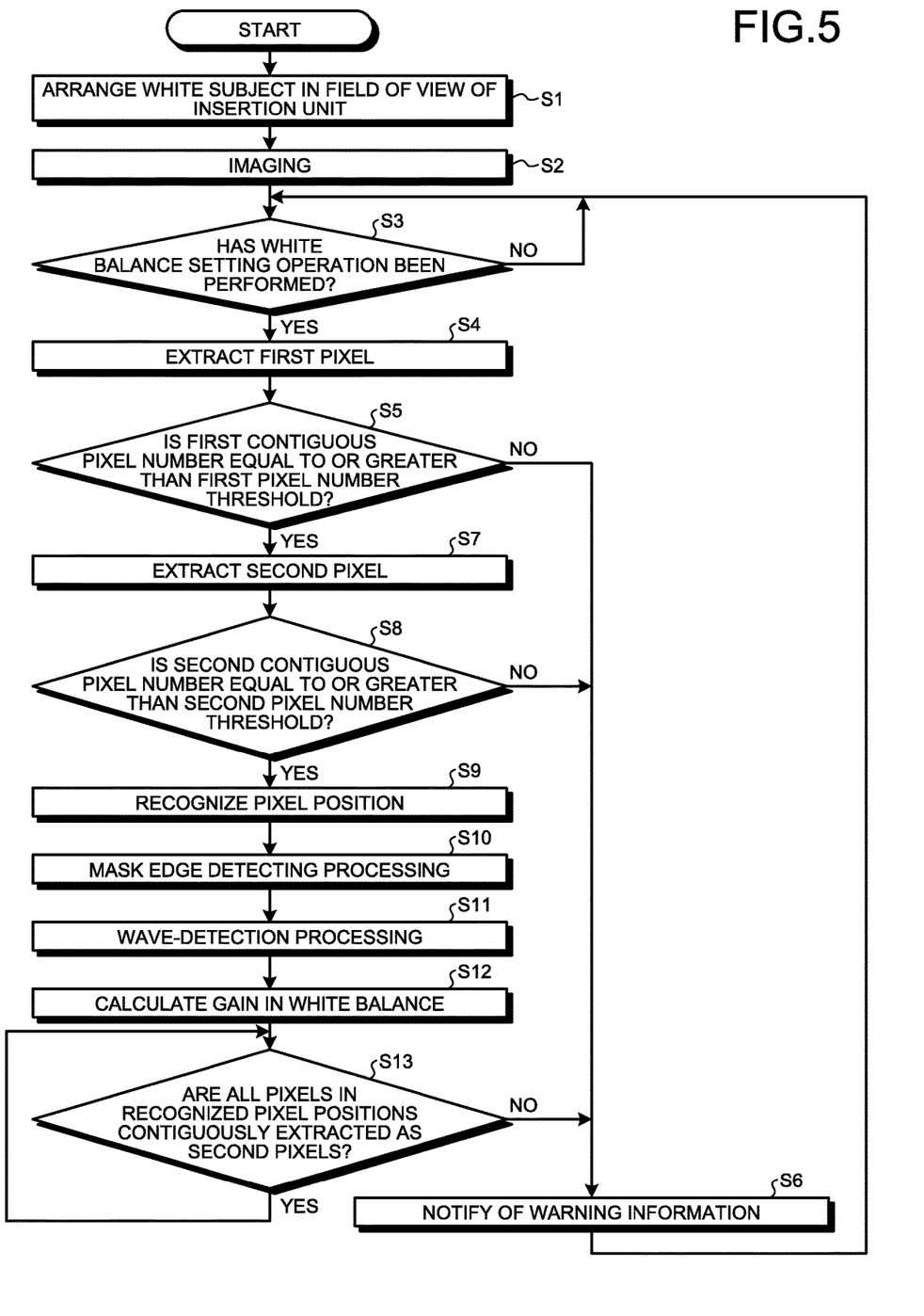
FIG. 5 is a flowchart that illustrates operation of the endoscope apparatus.
Figure 6:
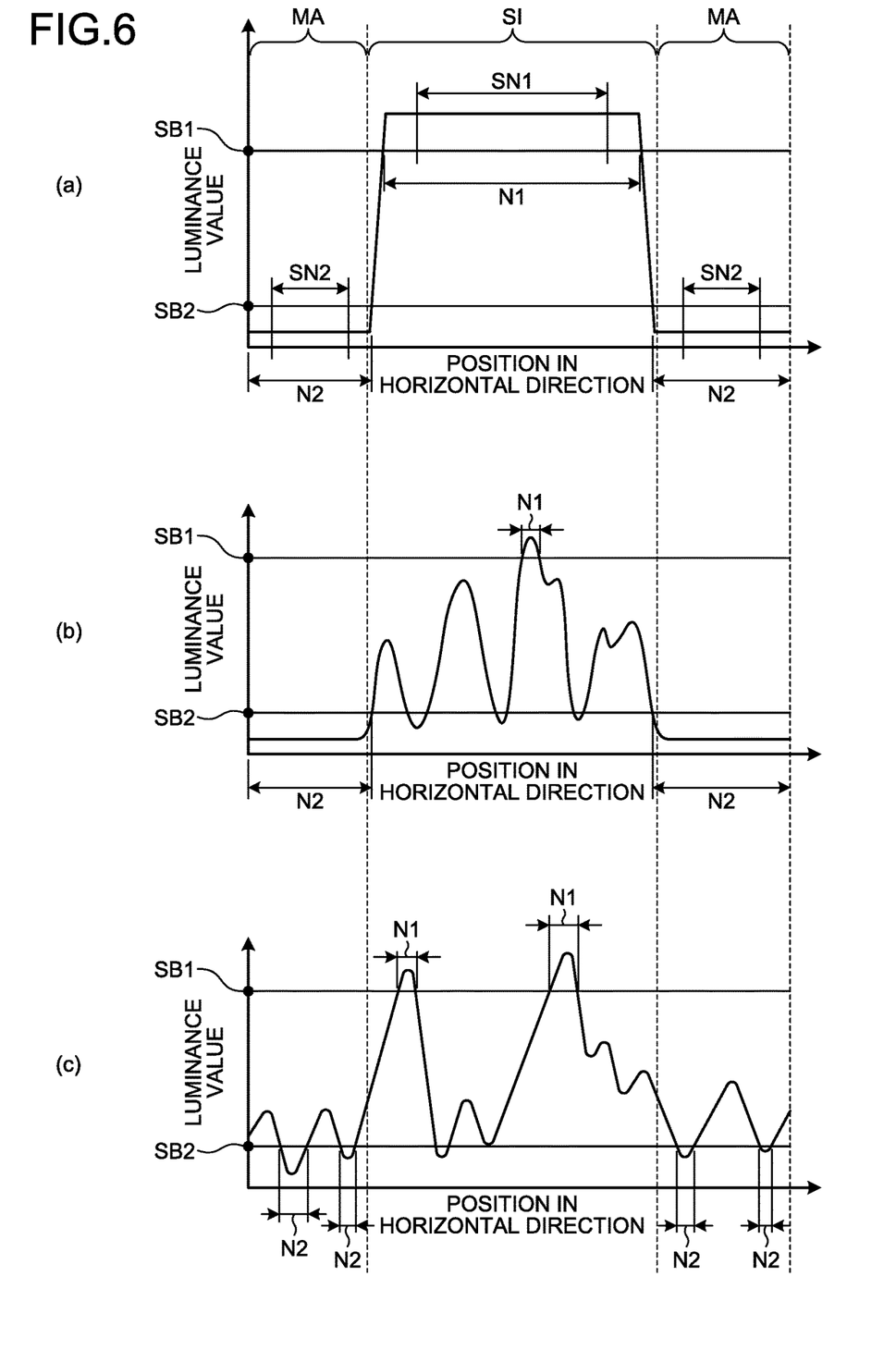
FIG. 6 is an illustrative drawing of operation of the endoscope apparatus.

Operation (a method of detecting an edge) of the above-described endoscope apparatus 1 will now be described. FIG. 5 is a flowchart that illustrates operation of the endoscope apparatus 1. FIG. 6 is an illustrative drawing of operation of the endoscope apparatus 1. More specifically, FIG. 6 is a drawing that illustrates distribution of luminance values on the horizontal line L7 positioned in the center of the captured image CI illustrated in (a) of FIG. 4. Operation of the edge processing unit 94, the wave-detection processing unit 93, the display control unit 95, and the display device 7 will be mainly described. A user, for example, a doctor puts a white subject such as gauze on the front end of the insertion unit 2 and arranges the subject in the field of view of the insertion unit 2 (Step S1: subject arranging step). The endoscope apparatus 1 starts imaging the subject (Step S2: imaging step).

After Step S2, the control unit 96 continuously monitors whether the input unit 97 receives the white balance setting operation (Step S3: operation receiving step). If the control unit 96 determines that no white balance setting operation is received (No at Step S3), the control unit 96 continues monitoring at Step S3. If the control unit 96 determines that the white balance setting operation has been received (Yes at Step S3), the extracting unit 942 acquires a luminance signal (Y signal) of image signals (Y, $C_B/C_R$ signals) processed by the image processing unit 92. The extracting unit 942 compares the luminance value of each pixel on the horizontal line L7 positioned in the center of the captured image CI with the first luminance threshold SB1 based on the luminance signal (Y signal) and extracts first pixels having a higher luminance value than the first luminance threshold SB1 (Step S4).

After Step S4, the processing possibility determining unit 943 compares the first contiguous pixel number N1 in which the first pixels extracted at Step S4 are contiguously aligned on the horizontal line L7 with the first pixel number threshold SN1 and determines whether the first contiguous pixel number N1 is equal to or greater than the first pixel number threshold SN1 (whether the image is in a processing possible state or in a processing impossible state) (Step S5). The processing possibility determining unit 943 thereafter outputs a signal according to the result of determination to the control unit 96.

(a) of FIG. 6 illustrates distribution of luminance values on the horizontal line L7 in the captured image CI with the insertion unit 2 connected to the camera head 5 and with a white subject arranged in the field of view of the insertion unit 2 at Step S1 (hereinafter referred to as a first state). In the first state, the subject image SI has a sufficiently high luminance value with the first contiguous pixel number N1 equal to or greater than the first pixel number threshold SN1. The image is therefore determined to be in a processing possible state at Step S5. (b) of FIG. 6 illustrates distribution of luminance values on the horizontal line L7 in the captured image CI with the insertion unit 2 connected to the camera head 5 and with no white subjects arranged in the field of view of the insertion unit 2 at Step S1 (hereinafter referred to as a second state). In the second state, the subject image SI has a great deal of variation among the luminance values with the first contiguous pixel number N1 less than the first pixel number threshold SN1. The image is therefore determined to be in a processing impossible state at Step S5. Furthermore, (c) of FIG. 6 illustrates distribution of luminance values on the horizontal line L7 in the captured image CI with no insertion units 2 connected to the camera head 5 (hereinafter referred to as a third state). In the third state, with the insertion unit 2 detached from the camera head 5, the entire captured image CI has a great deal of variation among the luminance values. As is the case with the second state, the image is determined to be in a processing impossible state at Step S5 with the first contiguous pixel number N1 less than the first pixel number threshold SN1.

If the processing possibility determining unit 943 determines that the first contiguous pixel number N1 is less than the first pixel number threshold SN1 (the image is in a processing impossible state) (No at Step S5), the apparatus may possibly be in the second or the third state. The boundary point BP thus may not be accurately detected in the mask edge detecting processing. The display control unit 95 has the display device 7 display a display image where an image (warning information) including a message such as "retry white balance setting operation" is overlapped on the captured image CI under control of the control unit 96 (Step S6). The endoscope apparatus 1 returns to Step S3.

If the processing possibility determining unit 943 determines that the first contiguous pixel number N1 is equal to or greater than the first pixel number threshold SN1 (the image is in a processing possible state) (Yes at Step S5), the extracting unit 942 acquires a luminance signal (Y signal) of image signals (Y, $C_B/C_R$ signals) processed by the image processing unit 92. The extracting unit 942 compares the luminance value of each pixel on the horizontal line L7 positioned in the center of the captured image CI with the second luminance threshold SB2 based on the luminance signal (Y signal) and extracts second pixels with a lower luminance value than the second luminance threshold SB2 (Step S7). In the subsequent steps, Step S7 is continuously performed in parallel with other processing.

After Step S7, the processing possibility determining unit 943 compares the second contiguous pixel number N2 in which the second pixels extracted at Step S7 are contiguously aligned on the horizontal line L7 with the second pixel number threshold SN2 and determines whether the second contiguous pixel number N2 is equal to or greater than the second pixel number threshold SN2 (whether the image is in a processing possible state or in a processing impossible state) (Step S8). The processing possibility determining unit 943 thereafter outputs a signal according to the result of determination to the control unit 96.

In the first and the second states, the insertion unit 2 is connected to the camera head 5. As illustrated in (a) and (b) of FIG. 6, the mask area MA has a sufficiently low luminance value with the second contiguous pixel number N2 equal to or greater than the second pixel number threshold SN2. The image is therefore determined to be in a processing possible state at Step S8. In the third state, the insertion unit 2 is not connected to the camera head 5. As illustrated in (c) of FIG. 6, the captured image CI has a great deal of variation among the luminance values with the second contiguous pixel number N2 less than the second pixel number threshold SN2. The image is therefore determined to be in a processing impossible state at Step S8.

If the processing possibility determining unit 943 determines that the second contiguous pixel number N2 is less than the second pixel number threshold SN2 (the image is in a processing impossible state) (No at Step S8), the apparatus may possibly be in the third state. The boundary point BP thus may not be accurately detected in the mask edge detecting processing. The endoscope apparatus 1 therefore moves back to Step S6. If the processing possibility determining unit 943 determines that the second contiguous pixel number N2 is equal to or greater than the second pixel number threshold SN2 (the image is in a processing possible state) (Yes at Step S8), the pixel position recognizing unit 944 recognizes the pixel position (each pixel position in the mask area MA) of each second pixel in which the second contiguous pixel number N2 used for determination in Step S8 is equal to or greater than the second pixel number threshold SN2 (Step S9).

After Step S9, the edge detecting unit 941 performs the mask edge detecting processing (Step S10: mask edge detecting step). After Step S10, the wave-detection processing unit 93 acquires luminance signals (Y signals) of image signals (Y, $C_B/C_R$ signals) processed by the image processing unit 92. The wave-detection processing unit 93 determines the area of the subject image SI surrounded by a plurality of boundary points BP detected at Step S9 to be a wave-detection area. The wave-detection processing unit 93 performs wave-detection processing based on a luminance signal (Y signal) of each pixel in the wave-detection area of the acquired luminance signals (Y signals) (Step S11) and outputs wave-detection information obtained by the wave-detection processing to the control unit 96. In the subsequent steps, Step S11 is continuously performed in parallel with other processing.

After Step S11, the parameter calculating unit 962 calculates respective gains by which the RGB values are multiplied in the white balance adjustment processing performed by the image processing unit 92 based on the wave-detection information output from the wave-detection processing unit 93 (Step S12: gain calculating step). The parameter calculating unit 962 outputs a control signal to the image processing unit 92 and determines the calculated gains to be gains by which the RGB values are multiplied in the white balance adjustment processing performed by the image processing unit 92. The parameter calculating unit 962 further calculates brightness parameters based on the wave-detection information.

After Step S12, the variation determining unit 945 determines whether all the pixels in the pixel positions recognized at Step S9 are contiguously extracted as the second pixels by the extracting unit 942 after Step S10 (Step S13). The variation determining unit 945 outputs a signal according to the result of determination to the control unit 96. If the apparatus transitions to the second state after undergoing the mask edge detecting processing in the first state, which means that the white subject has been merely removed from the front end of the insertion unit 2, there is no changes in the luminance value of each pixel in the mask area MA as seen from comparison between (a) of FIG. 6 and (b) of FIG. 6. Step S13 is therefore determined to be "Yes". If the apparatus transitions to the third state after undergoing the mask edge detecting processing in the first state, which means that the insertion unit 2 has been detached from the camera head 5, the entire captured image CI comes to have a great deal of variation among the luminance values. As seen from comparison between (a) of FIG. 6 and (c) of FIG. 6, some pixels in the pixel positions in the mask area MA recognized in the first state are not extracted as the second pixels (their luminance values are equal to or greater than the second luminance threshold SB2). Step S13 is therefore determined to be "No".

If the pixels are determined not to be contiguously extracted as the second pixels (No at Step S13), the apparatus has transitioned from the first state to the third state, and the insertion unit 2 may possibly be replaced by a different insertion unit 2 (for example, such an insertion unit 2 that has a different diameter and accordingly provides a subject image SI in the captured image CI having a different diameter). The endoscope apparatus 1 therefore moves back to Step S6. On the other hand, if the pixels are determined to be contiguously extracted as the second pixels (Yes at Step S13), the endoscope apparatus 1 continues Step S13.

The above-described embodiment exerts the following advantageous effects. The present disclosure is based on an action of a user, for example, a doctor, who uses a white subject such as gauze when having an endoscope apparatus 1 calculate a gain in white balance. The endoscope apparatus 1 according to the embodiment performs the mask edge detecting processing that detects a boundary point BP between a subject image SI and a mask area MA based on a luminance signal of each pixel in the captured image CI in response to the white balance setting operation. The endoscope apparatus 1 is able to perform the mask edge detecting processing in the first state in which a white subject such as gauze is used. With this process, the subject image SI included in the captured image CI has a sufficiently high luminance value, which allows more accurate detection of the boundary point BP between the subject image SI and the mask area MA using the luminance distribution in the captured image CI.

The endoscope apparatus 1 according to the embodiment determines whether the image is in a processing possible state or in a processing impossible state based on comparison between the luminance value and each of the first and the second luminance thresholds SB1 and SB2, comparison between the first contiguous pixel number N1 and the first pixel number threshold SN1, and comparison between the second contiguous pixel number N2 and the second pixel number threshold SN2. The endoscope apparatus 1 performs the mask edge detecting processing only when the image is determined to be in a processing possible state. With this configuration, the endoscope apparatus 1 may avoid performing the mask edge detecting processing in the second state, in which a subject other than a white subject such as gauze is used, and in the third state, in which the insertion unit 2 is detached from the camera head 5. In other words, the endoscope apparatus 1 may achieve effects of performing the mask edge detecting processing only in the first state and accurately detecting the boundary point BP between the above-described subject image SI and mask area MA in a preferred manner.

Furthermore, if the image is in a processing impossible state, the endoscope apparatus 1 according to the embodiment displays a display image where an image including a message such as "retry white balance setting operation" is overlapped on the captured image CI. This process enables the user such as a doctor to recognize that the apparatus is in the second or the third state. In other words, this process allows the apparatus to transition from the second or the third state to the first state and is able to have the user such as a doctor retry the white balance setting operation. The mask edge detecting processing may be performed in the first state, which may achieve effects of accurately detecting the boundary point BP between the above-described subject image SI and mask area MA in a preferred manner.

If the insertion unit 2 is replaced by another insertion unit 2 after the mask edge detecting processing and the calculation processing for calculating a gain in white balance, the calculation processing for calculating a gain in white balance needs to be performed again considering the individual variability between the insertion units 2. Furthermore, the insertion units 2 may have respective different diameters, and in this case, the mask edge detecting processing also needs to be performed again. The endoscope apparatus 1 according to the embodiment recognizes the pixel position of second pixels in which the second contiguous pixel number N2 is equal to or greater than the second pixel number threshold SN2 after determination of the image to be in a processing possible state and determines whether all the pixels in the recognized pixel positions are contiguously extracted as the second pixels (the second determination processing). Upon determination of "No", the endoscope apparatus 1 displays a display image where an image including a message such as "retry white balance setting operation" is overlapped on the captured image CI. The second determination processing allows determination of whether the apparatus has transitioned from the first state to the third state and whether the insertion unit 2 is in a state to be replaced by another insertion unit 2. The endoscope apparatus 1 is further able to have a user such as a doctor retry the white balance setting operation by displaying a display image where an image including a message such as "retry white balance setting operation" is overlapped on the captured image CI. The endoscope apparatus 1 is able to perform the calculation processing for calculating a gain in white balance and the mask edge detecting processing again on the replaced insertion unit 2.

The endoscope apparatus 1 according to a first embodiment performs wave-detection processing on a wave-detection area, which is the area of the subject image SI surrounded by a plurality of boundary points BP between the subject image SI detected by the mask edge detecting processing and the mask area MA. This configuration allows the wave-detection processing to be performed on the largest possible wave-detection area (substantially the entire area of the subject image SI) excluding the mask area MA. Processing (for example, AF processing and calculating processing for calculating a brightness parameter) based on wave-detection information obtained by the wave-detection processing may be therefore accurately performed.

Other Embodiments

The embodiment has been described; however, it should be noted that the present disclosure is not limited to the above-described embodiment. In the above-described embodiment, at least a part of the configuration (the lens unit 51, the lens driving unit 52, the lens position detecting unit 53, and the imaging unit 54) provided to the camera head 5 may be provided to the front end in the insertion unit 2. The insertion unit 2 is not limited to a rigid endoscope and may be a flexible endoscope. In the above-described embodiment, at least a part of the functions of the control unit 96 may be provided outside (to the camera head 5, the connectors CN1 and CN2) the control device 9. In the above-described embodiment, the operation receiving unit receiving the white balance setting operation according to the present disclosure is not necessarily provided to the control device 9 and may be provided to the camera head 5. In the above-described first embodiment, the warning information notifying unit 100 displays an image including a message such as "retry white balance setting operation"; however, the method is not limited thereto. The warning information notifying unit 100 may notify the user of the information by another method (for example, output the message in voice). In the above-described embodiment, the endoscope apparatus 1 may be used in the industrial field and observe the inside of a subject such as a mechanical structure.

The present disclosure is based on an action of a user, for example, a doctor, who uses a white subject such as gauze when having the endoscope calculate a gain in white balance. An endoscope apparatus according to the present disclosure performs mask edge detecting processing that detects a boundary point between a subject image and a mask area included in a captured image based on a luminance signal of each pixel in the captured image in response to a user operation for having a gain in white balance calculated. The endoscope apparatus is able to perform the mask edge detecting processing when the subject is a white subject such as gauze. This structure significantly increases the luminance value of the subject image included in the captured image, which allows more accurate detection of a boundary point between the subject image and the mask area using the luminance distribution on the captured image. Moreover, as is the case of the above-described endoscope apparatus, a method of detecting an edge according to the present disclosure is based on the above-described action of a user such as a doctor and exerts the same advantageous effects as those of the above-described endoscope apparatus.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscope apparatus comprising:
 a camera detachably connected to a base of an endoscope adapted to be inserted in a subject, the camera including a sensor configured to image a subject image captured by the endoscope; and
 circuitry configured to:
 process an image captured by the camera and generate a video signal for display;
 receive a user operation for calculating a gain in white balance;
 calculate the gain in white balance based on the captured image in response to the user operation;
 compare a luminance value based on a luminance signal of each pixel on a line in the captured image with a first luminance threshold and extract first pixels having a hither luminance value than the first luminance threshold;
 compare a first contiguous pixel number in which the first pixels are contiguously aliened on the line with a first pixel number threshold and determine whether the captured image is in a processing possible state that the first contiguous pixel number is equal to or greater than the first pixel number threshold or in a processing impossible state that the first contiguous pixel number is less than the first pixel number threshold; and
 on condition that the image is in the processing possible state, perform mask edge detecting processing for detecting a boundary point between the subject image and a mask area other than the subject image included in the captured image in response to the user operation.

2. The endoscope apparatus according to claim 1, wherein the circuitry is further configured to:
 compare a luminance value based on a luminance signal of each pixel on a line in the captured image with a second luminance threshold and extracts second pixels having a lower luminance value than the second luminance threshold;
 compare a second contiguous pixel number in which the second pixels are contiguously aligned on the line with a second pixel number threshold and determines whether the captured image is in a processing possible state that the second contiguous pixel number is equal to or greater than the second pixel number threshold or in a processing impossible state that the second contiguous pixel number is less than the second pixel number threshold; and
 perform the mask edge detecting processing on condition that the image is in the processing possible state.

3. The endoscope apparatus according to claim 1, wherein the circuitry is further configured to:
 issue warning information when the captured image is determined to be in the processing impossible state.

4. The endoscope apparatus according to claim 1, wherein the circuitry is further configured to:
   compare a luminance value based on a luminance signal of each pixel on a line in the captured image with a second luminance threshold and extracts second pixels having a lower luminance value than the second luminance threshold;
   recognize a pixel position of the second pixel in which a second contiguous pixel number having the second pixels contiguously aligned on the line is equal to or greater than a second pixel number threshold;
   determine whether all pixels in the pixel positions are contiguously extracted as the second pixels; and
   issue warning information when the pixels are not contiguously extracted as the second pixels.

5. The endoscope apparatus according to claim 1, wherein the circuitry is further configured to:
   perform wave-detection processing for calculating a brightness parameter used for changing brightness on the captured image
   based on a luminance signal of each pixel in an area on the captured image surrounded by the boundary point.

6. The endoscope apparatus according to claim 1, wherein the circuitry is further configured to:
   perform wave-detection processing for controlling the camera
   based on a luminance signal of each pixel in an area on the captured image surrounded by the boundary point.

7. A method of detecting an edge executed by the endoscope apparatus according to claim 1, the method comprising:
   arranging a white subject in a field of view of the endoscope;
   receiving a user operation for calculating a gain in white balance;
   imaging a subject image captured by the endoscope;
   calculating the gain in white balance based on the image captured during the imaging in response to the user operation; and
   detecting a boundary point between the subject image and a mask area other than the subject image included in the captured image based on a luminance signal of each pixel in the captured image in response to the user operation.

8. An endoscope apparatus comprising:
   a camera detachably connected to a base of an endoscope adapted to be inserted in a subject, the camera including a sensor configured to image a subject image captured by the endoscope; and
   circuitry configured to:
   process an image captured by the camera and generate a video signal for display;
   compare a luminance value based on a luminance signal of each pixel on a line in the captured image with a first luminance threshold and extract first pixels having a higher luminance value than the first luminance threshold;
   compare a first contiguous pixel number in which the first pixels are contiguously aligned on the line with a first pixel number threshold and determine whether the captured image is in a processing possible state that the first contiguous pixel number is equal to or greater than the first pixel number threshold or in a processing impossible state that the first contiguous pixel number is less than the first pixel number threshold; and
   on condition that the image is in the processing possible state, perform mask edge detecting processing for detecting a boundary point between the subject image and a mask area other than the subject image included in the captured image.

9. An endoscope apparatus comprising:
   a camera detachably connected to a base of an endoscope adapted to be inserted in a subject, the camera including a sensor configured to image a subject image captured by the endoscope; and
   circuitry configured to:
   process an image captured by the camera and generate a video signal for display;
   receive a user operation for calculating a gain in white balance;
   calculate the gain in white balance based on the captured image in response to the user operation;
   perform mask edge detecting processing for detecting a boundary point between the subject image and a mask area other than the subject image included in the captured image; and
   perform wave-detection processing for calculating a brightness parameter used for changing brightness on the captured image based on a luminance signal of each pixel in an area on the captured image surrounded by the boundary point in response to the user operation.

10. A method of detecting an edge executed by the endoscope apparatus according to claim 9, the method comprising:
    arranging a white subject in a field of view of the endoscope;
    receiving a user operation for calculating a gain in white balance;
    imaging a subject image captured by the endoscope;
    calculating the gain in white balance based on the image captured during the imaging in response to the user operation; and
    detecting a boundary point between the subject image and a mask area other than the subject image included in the captured image based on a luminance signal of each pixel in the captured image in response to the user operation.

11. An endoscope apparatus comprising:
    a camera detachably connected to a base of an endoscope adapted to be inserted in a subject, the camera including a sensor configured to image a subject image captured by the endoscope; and
    circuitry configured to:
    process an image captured by the camera and generate a video signal for display;
    perform mask edge detecting processing for detecting a boundary point between the subject image and a mask area other than the subject image included in the captured image; and
    perform wave-detection processing for calculating a brightness parameter used for changing brightness on the captured image based on a luminance signal of each pixel in an area on the captured image surrounded by the boundary point.

* * * * *